United States Patent [19]

Herrmann et al.

[11] Patent Number: 4,948,263
[45] Date of Patent: Aug. 14, 1990

[54] DEW-POINT SENSOR

[75] Inventors: Rainer Herrmann, Steinen; Dieter Funken, Lörrach, both of Fed. Rep. of Germany

[73] Assignee: Endress u. Hauser GmbH u. Co., Maulburg, Fed. Rep. of Germany

[21] Appl. No.: 204,628

[22] Filed: Jun. 9, 1988

[30] Foreign Application Priority Data

Jun. 16, 1987 [DE] Fed. Rep. of Germany ....... 3720189

[51] Int. Cl.$^5$ ............................................. G01N 25/68
[52] U.S. Cl. ........................................ 374/28; 374/16; 374/27
[58] Field of Search ................... 374/28, 27, 16, 21; 324/61 P, 689, 664

[56] References Cited

U.S. PATENT DOCUMENTS

| | | | |
|---|---|---|---|
| 2,435,895 | 2/1948 | McIlvaine | 374/21 |
| 3,937,059 | 2/1976 | Nisolle | 374/21 |
| 4,378,168 | 3/1983 | Kuisma et al. | 374/28 |
| 4,579,462 | 4/1986 | Rall et al. | 374/28 |
| 4,626,774 | 12/1986 | Regtien | 324/61 R |

FOREIGN PATENT DOCUMENTS

| | | |
|---|---|---|
| 2634274 | 2/1978 | Fed. Rep. of Germany ........ 374/28 |
| 3231534 | 3/1984 | Fed. Rep. of Germany . |
| 221282 | 4/1985 | Fed. Rep. of Germany ... 324/61. R |
| 3446277 | 6/1986 | Fed. Rep. of Germany . |
| 2126350 | 3/1984 | United Kingdom ................. 374/28 |

*Primary Examiner*—William A. Cuchlinski, Jr.
*Assistant Examiner*—W. Morris Worth
*Attorney, Agent, or Firm*—Barnes & Thornburg

[57] ABSTRACT

A dew-point sensor for a dew-point measuring device for measuring the water vapor dew point in gases comprises a sensor surface which is exposed to the gas to be measured and on which on cooling to the dew-point temperature water vapor condenses. Mounted on the sensor surface are two electrode structures which comprise electrode portions which are arranged a uniform interval parallel to each other and which are covered with a moisture-insensitive insulating layer. The reaching of the dew-point temperature is determined by measuring the impedance or capacitance between the two electrode structures. The distance between the electrode portions, arranged parallel to each other, of the two electrode structures is of the order of magnitude of the diameter of the largest condensation droplet forming on reaching the dew-point temperature, or smaller than said diameter, and the thickness of the insulating layer is small compared with the distance between the electrode portions.

4 Claims, 2 Drawing Sheets

DEW-POINT SENSOR

The invention relates to a dew-point sensor for a dew-point measuring device for measuring the water vapour dew point in gases, comprising a sensor surface which is exposed to the gas to be measured and on which on cooling to the dew-point temperature water vapour condenses and two electrode structures mounted on the sensor surface and comprising electrode portions which are arranged at uniform distance apart parallel to each other and are covered with a moisture-insensitive insulating layer, the reaching of the dew-point temperature being determined by measuring the impedance or capacitance between the two electrode structures.

In known dew-point sensors of this type the distance between the electrode portions of the two electrode structures is at least 200 $\mu$m. This distance is substantially greater than the diameter of the first condensation droplets which form when the dew-point temperature is reached. The detection of the dew-point temperature is based on the fact that on formation of a dew layer because of the greater dielectric constant of water the capacitance between the two electrode structures changes. By regulating the temperature of the dew-point sensor an attempt is made to maintain a constant capacitance and thus a constant thickness of the dew layer. The temperature adjusted in this manner is measured as dew-point temperature.

With these known dew-point sensors it is not possible to detect the start of the condensation commencing when the dew-point temperature is reached because the first condensation droplets forming do not yet lead to any clearly distinguishable capacitance change. Furthermore, in particular soiling of the sensor surface greatly affects the measurement result because it can change the dielectric constant of the dew layer.

The problem underlying the invention is to provide a dew-point sensor of the type mentioned at the beginning with which the condensation starting on reaching the dew-point temperature can be detected immediately and which is very insensitive to soiling of the sensor surface.

According to the invention this problem is solved in that the distance between the electrode portions arranged parallel to each other of the two electrode structures is of the order of magnitude of the diameter of the largest condensation droplets forming on reaching the dew-point temperature or less than said diameter and that the thickness of the insulating layer is small compared with the distance between the electrode portions.

The dew-point sensor constructed according to the invention utilizes the fact that on reaching the dew-point temperature condensation droplets of a minimum size form within a very short time. The condensation droplets arising thus form a bridge between the thin insulating layers covering adjacent electrode portions. Since the ohmic resistance of said condensation droplets is small the capacitances, themselves independent of moisture, of the insulating layers are connected by a conductive bridge and because of the small thickness of said insulating layers said capacitances are large compared with the capacitance between the electrodes. The result of this is that the impedance or capacitance measured between the two electrode structures changes abruptly. This enables the first occurrence of condensation droplets to be clearly detected. This phenomenon is independent of the dielectric constant of the water in the condensation droplets. The dew-point sensor is therefore substantially more sensitive in the detection of the dew point and less sensitive to soiling than dew-point sensors in which the capacitance change caused by the dielectric constant of the dew layer is used for the dew-point detection.

Preferred embodiments and further developments of the dew-point sensor according to the invention are characterized in the subsidiary claims.

Further features and advantages of the invention will be apparent from the following description of an example of embodiment which is shown in the drawings, wherein.

Figure 1:
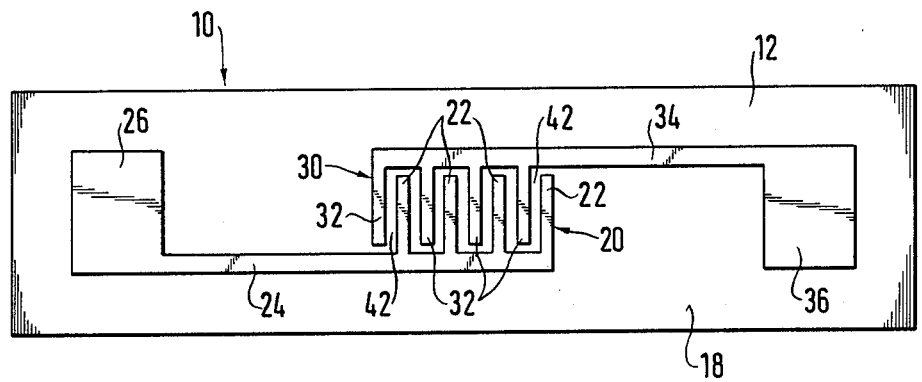
FIG. 1 is a plan view of a dew-point sensor made according to the invention.
Figure 2:
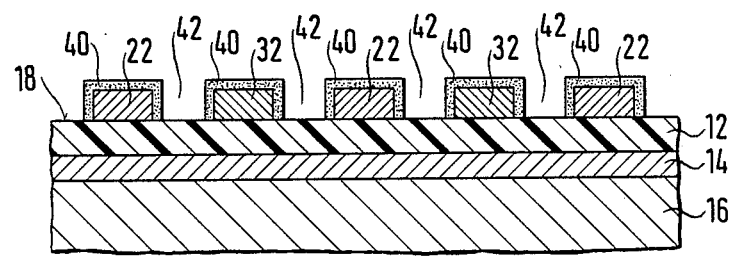
FIG. 2 is a section through part of the dew-point sensor of FIG. 1 to a larger scale.

The dew-point sensor 10 shown in FIG. 1 in plan view and in FIG. 2 partially in sectional view comprises a support 12 which consists of a moisture-insensitive insulating material. As can be seen, the support 12 is mounted with interposition of a separating disc 14 of aluminium on a Peltier element 16 with the aid of which it can be cooled to the dew-point temperature. The free upper side of the support 12 remote from the separating disc forms the sensor surface 18 which is exposed to the gas atmosphere of which the water vapour dew point is to be determined so that on cooling to the dew-point temperature a dew layer forms on said surface by condensation.

Formed on the sensor surface 18 are two electrode structures 20 and 30 which are illustrated in FIG. 1 in very simplified form for clarity. The electrode structure 20 has the form of a comb having a plurality of parallel teeth 22 which are connected at one end to a web 24 extending perpendicularly thereto. At the end of the web 24 a widened contact pad 26 is formed which serves for contacting a terminal conductor via which the electrode structure 20 is connected to the electronic circuit (not shown) of the dew-point measuring device in which the dew-point sensor is used. The electrode structure 30 consists in completely identical manner but in laterally inverted arrangement of teeth 32, a web 34 and a contact pad 36.

The teeth 22 and 32 of the two electrode structures lie in a small central region of the support 12 which forms the actual sensor region sensitive for the measuring operation. The teeth 22 and 32 are arranged alternately engaging in each other, the teeth 22 of the electrode structure 20 lying in the intermediate spaces between the teeth 32 of the electrode structure 30 and conversely the teeth 32 of the electrode structure 30 lying in the intermediate spaces between the teeth 22 of the electrode structure 20. Thus, the pairs of parallel adjacent teeth represent electrode portions belonging to different electrode structures The intermediate spaces between the teeth of each electrode structure are so wide that in each intermediate space a tooth of the other electrode structure can be accommodated with adequate spacing from the two adjacent teeth. This is apparent in particular from FIG. 2 which shows to a scale larger than the illustration of FIG. 1 a section through several adjacent teeth 22, 32 of the two electrode structures 20 and 30 respectively.

Each tooth 22 and 32 of the two electrode structures 20, 30 is coated with a moisture-insensitive insulating layer 40 which completely covers all the free faces of the tooth. The teeth 22 and 32 are thus separated firstly by the insulating material of the support 12 and secondly by the insulating layer 40 completely from the gas atmosphere of which the dew point is to be measured. In the embodiment illustrated in FIG. 2 a gap 42 extending up to the surface of the support 12 is present between the insulating layers covering two adjacent teeth.

The electrode structures 20 and 30 and the insulating layer 40 covering the teeth may be made on the support 12 by one of the usual methods which are known in the art of integrated circuits and from printed circuit board technology. The electrode structures 20, 30 are for example made photolithographically from a suitable metal coating, for example from tantalum or platinum. The insulating layer 40 must consist of a chemically stable electrically insulating and completely moisture-insensitive material. This can be glass, resist or another suitable metal oxide. The material of the insulating layer can also be applied by one of the known methods to the electrode structures. If the oxide of the metal used for the electrode structures 20, 30 has the necessary properties the insulating layer 40 may also possibly be formed by surface oxidation of the conductor metal.

Figure 3:
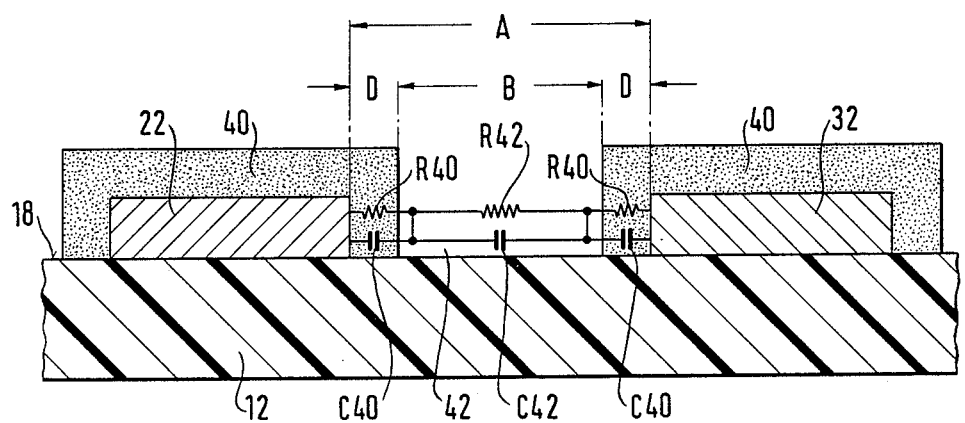
FIG. 3 is a schematic illustration of part of the dew-point sensor to a still greater scale and FIG. 4 shows the electrical equivalent circuit diagram of the dew-point sensor of FIG. 1.
Figure 4:
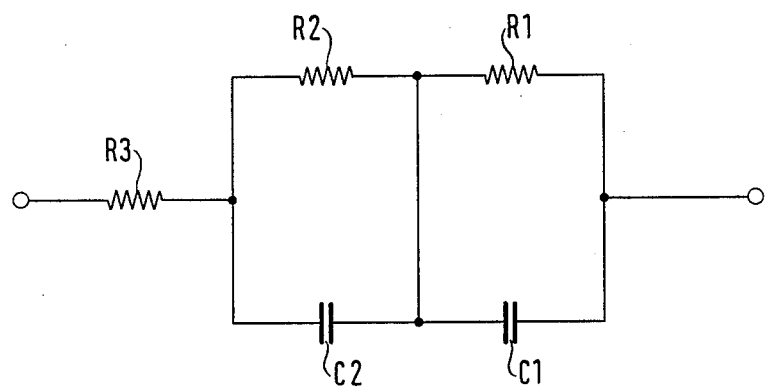

The mode of operation of the dew-point sensor of FIGS. 1 and 2 will be explained with the aid of FIGS. 3 and 4. FIG. 3 shows schematically in a sectional view similar to that of FIG. 2 but to a greater scale two adjacent teeth 22 and 32 with their insulating layers 40. The thickness D of the insulating layers 40 is exaggerated in FIG. 3; in reality it is small compared with the distance A between two adjacent teeth 22 and 32. Accordingly, the width B of the gap 42 is in reality only slightly smaller than the distance A between the teeth. Furthermore, FIG. 3 also shows the circuit symbols of the electrical quantities essential to the mode of operation. FIG. 4 is an electrical equivalent circuit diagram of the impedance of the two electrode structures 20 and 30 governed by said electrical quantities.

For the electrical behaviour of the dew-point sensor the electrical parameters of the path between every two adjacent teeth 22, 32 of the two electrode structures 20, 30 are decisive. This path is made up of three sections having impedances connected in series:

the insulating layer 40 on the tooth 22 with an electrical impedance which can be represented by a parallel circuit comprising a resistor R40 and a capacitance C40;

the gap 42 having an electrical impedance which can be represented by a parallel circuit comprising a resistor R42 and a capacitance C42;

the insulating layer 40 on the tooth 32 having an electrical impedance which can again be represented by a parallel circuit comprising a resistor R40 and a capacitance C40.

The parallel circuit of all these partial impedances between the teeth of the two electrode structures gives the total impedance of the two electrode structures which is represented by the equivalent circuit diagram of FIG. 4. The resistor R1 corresponds to the parallel circuit of all the gap resistances R42 and the capacitance C1 corresponds to the parallel circuit of all the gap capacitances C42. For simplification the parallel circuits of the two layer resistances R40 lying in series is represented by a single resistor R2 and the parallel circuits of the two layer capacitances C40 lying in series by a single capacitance C2. The resistor R3 denotes the resistance of the metal layers of the conductor structures 20 and 30.

The dew-point detection is based on determining the change in the total impedance occurring when the dew-point temperature is reached, this being caused by condensation droplets starting to form on the sensor surface 18. The change in the total impedance thus depends on the influence of the condensation droplets on the values of the circuit elements of the equivalent circuit diagram of FIG. 4.

Since the material of the insulation layer 40 is moisture-insensitive, the values of the resistance R2 and the capacitance C2 are not changed by condensation. Similarly, the resistance R3 of the electrode structures is independent of any condensation formation.

The sole circuit components having values influenced by the dew-point condensation are the resistance R1 and the capacitance C1 of the gaps between the teeth. The following observations apply to these electrical quantities:

In the dry state of the dew-point sensor, i.e. at temperatures above the dew-point temperature, the values of the resistance R1 and of the capacitance C1 depend on the gas disposed in the gaps 42. The resistance R1 thus has a very high value which is of the same order of magnitude as the insulation resistance R2. The capacitance C1 is small compared with the capacitance C2 of the insulating layer 40 because the thickness D of the insulating layer 40 is very small compared with the width B of the gap 42. It should be remembered that in FIG. 3 the thickness D of the insulating layer 40 has been exaggerated for clarification.

On cooling to the dew-point temperature within a very short time dew droplets of a minimum size form on the entire sensor surface 18 and thus of course also in each gap 42. On further cooling to temperatures beneath the dew-point temperature these droplets become larger and finally join up to form a continuous dew layer. It is important for an exact as possible a detection of the dew-point temperature to detect the first condensation of the dew droplets. This is achieved by a particular dimensioning of the width B of the gap 42: said width B corresponds to the minimum diameter of the dew droplets forming in very short time by condensation so that the first dew droplets which condense when the dew-point temperature is reached immediately fill the entire width of the gap 42. Since the resistance of the dew droplets is several orders of magnitude smaller than the resistance of the gas on occurrence of the condensation a sudden reduction of the resistance R1 to a value several times smaller results. At the same time the capacitance C1 increases somewhat corresponding to the greater dielectric constant of water but this increase is of no appreciable significance compared with the simultaneous reduction of the resistance R1.

These phenomena give the following effects on the measured impedance of the dew-point sensor:

In the dry state (above the dew-point temperature) with an adequately high measuring frequency the impedance measured depends essentially on the series circuit comprising the two capacitances C1 and C2. The high resistances R1 and R2 lying in parallel therewith are comparatively negligible and the low series resistance R3 can be disregarded. Since furthermore the capacitance C2 is large compared with the capacitance C1 the impedance measured is governed primarily by the capacitive reactance of the capacitance C1.

On reaching the dew-point temperature the resistance R1 suddenly assumes a very much smaller value which now lies in series with the capacitance C2. The impedance measured then depends primarily on the capacitive reactance of the capacitance C2. Compared with the capacitance reactance of the capacitance C1 measured primarily in the dry state a pronounced impedance jump occurs with the first droplet formation and clearly designates reaching of the dew-point temperature. On still further reduction of the temperature below the dew-point temperature the resistance R1 admittedly decreases further but the capacitance C2, which primarily determines the impedance measured, remains unchanged so that the measured impedance does not appreciably change any more.

Greatly simplified the mechanism outlined may be represented by considering the drop formation on dew-point condensation to establish a "short-circuit" between the two capacitances C40. Decisive for this effect is the correct dimensioning of the width B of all the gaps 42 which must correspond to the droplet diameter forming in extremely short time. Investigations have shown that the effect outlined occurs only when the width B is less than about 40 μm; preferably, it should be of the order of magnitude of about 20 μm. It is further important for the thickness of the insulating layer 40 to be small compared with the width B of the gap 42 dimensioned in this manner.

In an embodiment which has been tried in practice of a dew-point sensor of the type described the electrode structures 20, 30 consist of tantalum which is applied to a support 12 of aluminium oxide. Each electrode structure has a comb of 50 teeth with a width of 21 μm and a length of 2 mm. The spacing between the interengaging teeth of the two electrode structures is 19 μm. The actual sensor region formed by the two interengaging comb structures thus occupies an area of only 2×4 mm. The insulating layer 40 consists of highly compacted and thus moisture-insensitive tantalum oxide which is formed in a thickness of 160 nm by surface oxidation of the tantalum of the electrode structures.

By suitable dimensioning of the measuring frequency the optimum ratio can be obtained between the impedances measured in the various conditions so that the impedance jump on reaching the dew-point temperature is particularly pronounced. A measuring frequency of about 100 kHz has proved suitable.

It is of course possible to carry out a pure capacitance measurement instead of the impedance measurement. In this case in the dry state essentially the capacitance C1 is measured and on reaching the dew-point temperature the capacitance value measured suddenly changes to the value of the capacitance C2. However, it must be remembered that this capacitance jump is not due to a change of a physical capacitance but due to the short-circuit-like bridging following the sudden change of the physical resistance R1.

Instead of the comb structures other electrode structures may be used having electrode portions arranged at the specified distance apart parallel to each other, for example meander or grid structures The electrode portions may also be curved, for example spiral or in the form of concentric arcs.

We claim:

1. A dew-point sensor for a dew-point measuring device for measuring the water dew-point in gases, comprising:
    a sensor surface which is exposed to the gas to be measured;
    means for cooling said sensor surface to a dew-point temperature at which water vapor condenses on said sensor surface;
    a first electrode structure having a first electrode portion mounted on said sensor surface;
    a second electrode structure having a second electrode portion mounted on said sensor surface at a uniform distance of less than 50 μm from said first electrode portion;
    a moisture-insensitive insulating layer covering said first electrode portion and said second electrode portion and having a thickness smaller than said uniform distance between said first and second electrode portions to maintain a gap between said electrode portions; and
    whereby the insulating layer forms a parallel capacitance-resistance in series with the capacitance-resistance between the electrodes and the electrode resistance such that formation of condensed droplets fill the gap between electrode portions to cause a large change of the impedance or capacitance between the two electrode structures when the dew-point temperature is reached.

2. The apparatus of claim 1 wherein said uniform distance between said first electrode portion and said second electrode portion is about 20 μm.

3. The apparatus of claim 2 wherein said moisture insensitive insulating layer is less than 1 μm thick.

4. The apparatus of claim 1 wherein said first electrode portion has a series of teeth and said second electrode portion has a series of teeth intermeshing with the series of teeth of the first electrode portion.

* * * * *

UNITED STATES PATENT AND TRADEMARK OFFICE
CERTIFICATE OF CORRECTION

PATENT NO. : 4,948,263

DATED : August 14, 1990

INVENTOR(S) : Herrmann et al.

It is certified that error appears in the above-identified patent and that said Letters Patent is hereby corrected as shown below:

On the bibliography page, under "Foreign Patent Documents", please insert --Silicon Dew-Point Sensor for Accurate Humidity Measurement Systems, Regtien, Delft Univ. Press 1981, pp.32-33--

Signed and Sealed this

Tenth Day of December, 1991

Attest:

HARRY F. MANBECK, JR.

*Attesting Officer*　　　　　*Commissioner of Patents and Trademarks*